United States Patent
Sudo et al.

(10) Patent No.: US 9,637,405 B2
(45) Date of Patent: May 2, 2017

(54) EVALUATION METHOD OF SUITABLE SILICA POWDER IN MANUFACTURING VITREOUS SILICA CRUCIBLE FOR PULLING OF SILICON SINGLE CRYSTAL

(71) Applicant: SUMCO CORPORATION, Minato-ku, Tokyo (JP)

(72) Inventors: Toshiaki Sudo, Akita (JP); Tadahiro Sato, Akita (JP); Ken Kitahara, Akita (JP); Makiko Hinooka, Akita (JP)

(73) Assignee: SUMCO CORPORATION, Tokyo (JP)

( * ) Notice: Subject to any disclaimer, the term of this patent is extended or adjusted under 35 U.S.C. 154(b) by 0 days.

(21) Appl. No.: 14/901,034

(22) PCT Filed: Jun. 30, 2013

(86) PCT No.: PCT/JP2013/067947
§ 371 (c)(1),
(2) Date: Dec. 27, 2015

(87) PCT Pub. No.: WO2015/001592
PCT Pub. Date: Jan. 8, 2015

(65) Prior Publication Data
US 2016/0200617 A1 Jul. 14, 2016

(51) Int. Cl.
*C30B 15/10* (2006.01)
*G01N 15/08* (2006.01)
(Continued)

(52) U.S. Cl.
CPC .............. *C03B 1/00* (2013.01); *C03B 19/095* (2013.01); *G01N 21/55* (2013.01); *G02B 21/008* (2013.01); *C30B 15/10* (2013.01); *C30B 29/06* (2013.01); *G01N 15/088* (2013.01); *G01N 2015/0015* (2013.01); *G01N 2015/0096* (2013.01); *G01N 2033/0091* (2013.01); *Y02P 40/57* (2015.11)

(58) Field of Classification Search
CPC ........ C03B 15/10; C03B 15/10; G01N 15/088
See application file for complete search history.

(56) References Cited

U.S. PATENT DOCUMENTS

2011/0181701 A1* 7/2011 Varslot .................. G06T 7/0024
348/46

FOREIGN PATENT DOCUMENTS

| JP | 2009007211 A | 1/2009 |
|----|--------------|--------|
| JP | 2010143818 A | 7/2010 |

(Continued)

OTHER PUBLICATIONS

International Search Report (ISR) mailed Jul. 23, 2013, issued for International application No. PCT/JP2013/067947.

*Primary Examiner* — Erin Snelting
(74) *Attorney, Agent, or Firm* — Law Office of Katsuhiro Arai

(57) ABSTRACT

An evaluation method of suitable silica powder for forming a bubble-free layer of a vitreous silica crucible for pulling of a silicon single crystal, includes: a process of measuring a porosity between silica particles in the silica powder, a process of melting the silica powder, a process of measuring a bubble content rate of a vitreous silica block obtained by cooling to harden the melted silica powder, and a process of determining whether the silica powder is suitable from the porosity of the silica powder and the bubble content rate of the vitreous silica block.

8 Claims, 2 Drawing Sheets

(51) Int. Cl.
  *C03B 1/00* (2006.01)
  *G01N 21/55* (2014.01)
  *G02B 21/00* (2006.01)
  *C03B 19/09* (2006.01)
  *C30B 29/06* (2006.01)
  *G01N 15/00* (2006.01)
  *G01N 33/00* (2006.01)

(56) References Cited

FOREIGN PATENT DOCUMENTS

| | | | |
|---|---|---|---|
| JP | 2012116716 | A | 6/2012 |
| JP | 2012211070 | A | 11/2012 |
| JP | 2013120138 | A | 6/2013 |

\* cited by examiner

EVALUATION METHOD OF SUITABLE SILICA POWDER IN MANUFACTURING VITREOUS SILICA CRUCIBLE FOR PULLING OF SILICON SINGLE CRYSTAL

This application is the U.S. National Phase under 35 U.S.C. §371 of International Application PCT/JP2013/067947, filed Jun. 30, 2013. The International Application was published under PCT Article 21(2) in a language other than English.

TECHNICAL FIELD

The present invention relates to an evaluation method of suitable silica powder in manufacturing vitreous silica crucible for pulling of a silicon single crystal.

BACKGROUND ART

A silicon single crystal by the Czochralski method is manufactured using a vitreous silica crucible. The silicon single crystal is manufactured by melting high-purity polysilicon to obtain a silicon melt, pulling up while rotating a seed crystal with the tip of the seed crystal contacted with the surface of the silicon melt. In order to maintain a solid-liquid interface of the silicon melt central part, which is contacted with the single crystal, to be near the silicon melting point of 1420° C., the temperature of the vitreous silica crucible is as high as about 1450-1600° C. In pulling of silicon single crystal which can last 2 weeks, the extent of deformation of a sidewall sagging at a rim portion of the vitreous silica crucible may be 5 cm or more.

The size of the vitreous silica crucible is, 28 inches (about 71 cm), 32 inches (about 81 cm), 36 inches (about 91 cm), and 40 inches (about 101 cm) etc., in diameter. A crucible with a diameter of 101 cm is an enormous crucible having a weight of about 120 kg, and the mass of silicon melt contained therein is 900 kg or more. That is, during the pulling of silicon single crystal, 900 kg or more silicon melt of about 1500° C. is contained in the crucible.

Such vitreous silica crucible is suitable for manufacturing a large-size single-crystal silicon ingot with a diameter of 200 to 450 mm (for example: 200 mm, 300 mm, 450 mm) and a length from 1 m to 5 m or more. A single-crystal silicon wafer manufactured from such large-size ingot is suitable for manufacture of flash memory or DRAM.

A silicon wafer used for manufacture of semiconductors is obtained by slicing a silicon single crystal. With the high integration of semiconductor devices in recent years, the reduction of void defects in the surface of a silicon wafer is in demand.

It is known that void defects can be removed by etching the wafer surface layer, but the production of a silicon single crystal without void defects is desired from the electronics field because the etching process is time-consuming and costly.

Various methods are known to produce a silicon single crystal without void defects. One is a method of reducing the bubbles in the transparent layer of a vitreous silica crucible for pulling of the silicon single crystal. The vitreous silica crucible for pulling of the silicon single crystal is manufactured using a silica powder. According to the rotating mold method, the vitreous silica crucible is manufactured by processes of (1) depositing silica powder in a rotating mold, and (2) melting the silica powder by arc discharge. The mixing of bubbles in the silicon single crystal is considered to be one cause of void defects. Therefore, in order to avoid bubbles mixing into the silicon single crystal, a transparent layer of the vitreous silica crucible is formed from a layer without bubbles.

In order to manufacture a vitreous silica crucible having a transparent layer, that is, a substantially bubble-free layer, a manufacture method of vitreous silica crucible using a rotating mold capable of sucking out the gas component inside the mold is known. Specifically, it is a method of depositing a silica powder on the inner face of the mold and then arc melting while exhausting the gas component by a suction apparatus (Patent Literature 1). Furthermore, Patent Literature 2 discloses a method of determining whether or not a cause of bubbles in the vitreous silica material exists.

BACKGROUND ART LITERATURES

Patent Literatures

Patent Literature 1: Japanese Patent Application Laid-Open 2010-143818
Patent Literature 2: Japanese Patent Application Laid-Open 2009-007211

SUMMARY OF THE INVENTION

Problems to be Solved by the Invention

However, even in the method disclosed in Patent Literature 1, there are cases where a bubble-free layer can be generated and cannot be generated, and it is difficult to stabilize the quality.

The reason for unstable quality has not been identified thus far, so the determination of quality cannot be made until a vitreous silica crucible is manufactured.

In view of such circumstances, the present invention provides an evaluation method of the silica powder which can be used to manufacture a stable vitreous silica crucible with a bubble-free layer.

Means for Solving the Problems

To solve the aforementioned problems, the present invention provides an evaluation method as follows. That is, an evaluation method of suitable silica powder in forming a bubble-free layer of a vitreous silica crucible for pulling of a silicon single crystal, includes: a process of measuring a porosity between the silica particles in the silica powder; a process of melting the silica powder; a process of measuring a bubble content rate of a vitreous silica block obtained by cooling to harden the melted silica powder; and a process of determining whether the silica powder is suitable from the porosity of the silica powder and the bubble content rate of the vitreous silica block.

The evaluation of whether the silica powder is suitable for the formation of the bubble-free layer of the vitreous silica crucible can be carried out by producing the vitreous silica crucible on a trial basis. However, since manufacturing a vitreous silica crucible takes time and is costly, in general, the bubble content rate of a silica block made by melting a silica powder is measured, and an evaluation of suitability of silica powder is performed (Patent Literature 2) (hereinafter, the conventional evaluation method). The conventional evaluation method is generally as follows: a silica powder is supplied in a heat-resistant container, the silica powder is melted in a vacuum atmosphere, then a bubble content rate of a vitreous silica block obtained by hardening the melted silica powder is measured. However, the silica powder evaluated to be suitable by this method is used to produce a vitreous silica by the Verneuil process using an oxyhydrogen flame melting, but if it is used in the manufacturing of a vitreous silica crucible by an arc melting, a good result may not be obtained. In this method, water vapor as a combustion gas from the oxyhydrogen burner is included in the vitreous silica which causes bubbles to generate when used in a silicon single-crystal pulling.

The present inventors have made an analysis of the silica powder which can result in a vitreous silica block with low bubble content. Initially, a result was such that the average particle diameter of the silica powder correlates to the bubble content rate of the vitreous silica block. However, it was found that, depending on the silica powder, in spite of the same average particle diameter, the bubble content rate of the vitreous silica block is either high or low, and variations occur in the results. As a result of detailed analysis, it was found that silica powder having variations in results has a different porosity of silica particles before melting. That is, if the shapes of the particles are different, for example, the way of filling (the filled state) changes even if the average particle diameter is the same.

Based on such a surprising discovery, the present inventors have concluded that whether a silica powder is suitable cannot be evaluated by simply measuring the bubble content of the vitreous silica block after melting. That is, it is concluded that it is necessary to consider not only the bubble content rate of the vitreous silica block after melting, but also voids within the silica powder before melting. As a result of further studies, the present inventors have found that a silica powder having a bubble content rate of a vitreous silica block in a prescribed range with respect to a porosity between silica particles, is suitable for forming a bubble-free layer of a vitreous silica crucible for pulling of silicon single crystal, and completed the present invention. By using the evaluation method of the present invention, it is possible to identify in advance a silica powder that generates no bubbles in the transparent layer.

MODES FOR CARRYING OUT THE INVENTION

Figure 1:
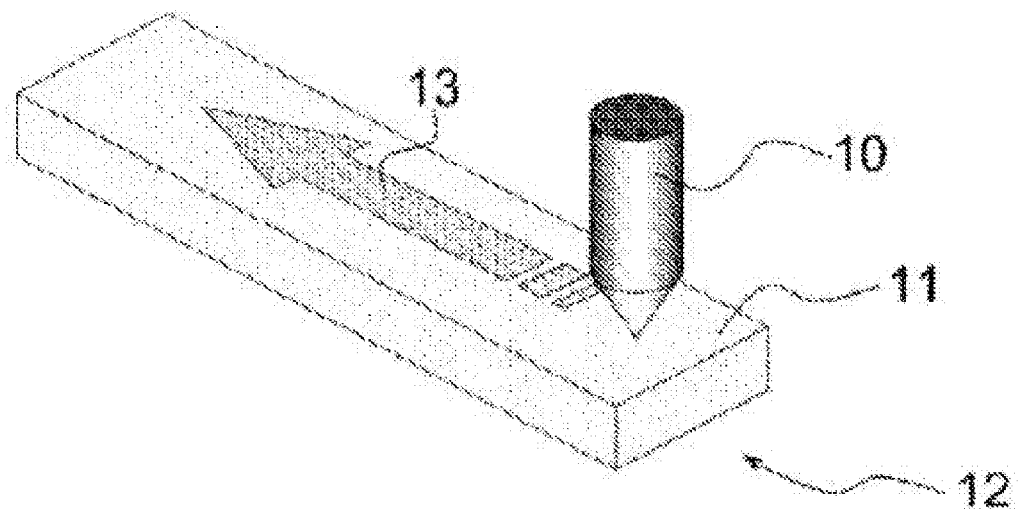
FIG. 1 is a schematic view showing a state of an objective lens 10 scanning on a surface 11 of a deposited silica powder.
Figure 2:
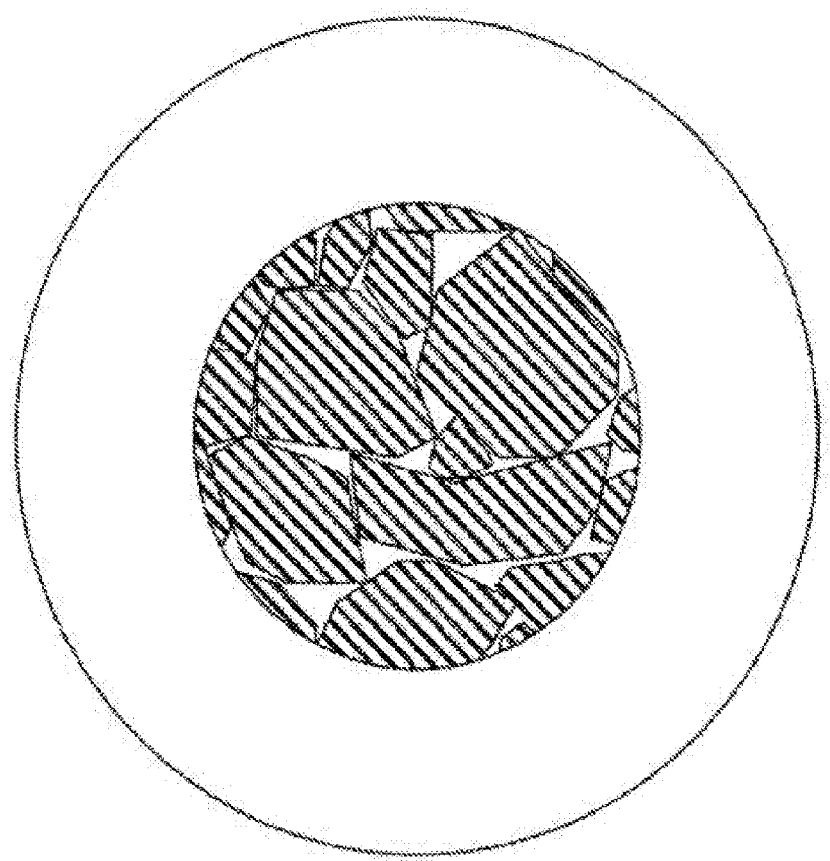
FIG. 2 is a conceptual diagram of a silica powder in a heat-resistant container. It is shown that the shaded areas are silica particles, and the white areas are gaps.
Figure 3:
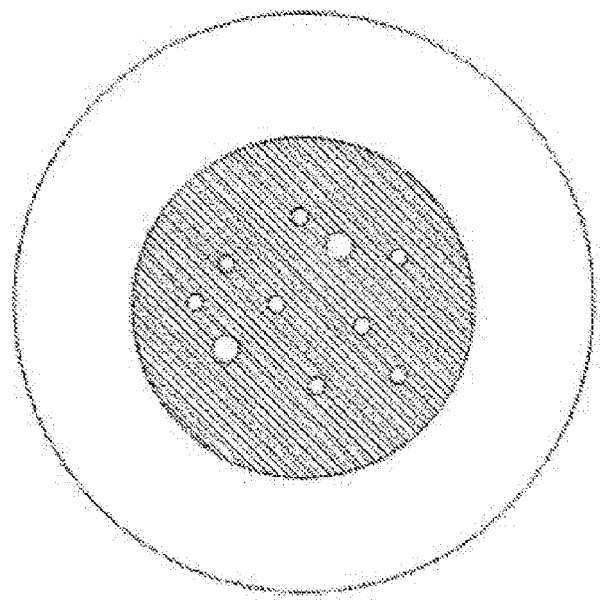
FIG. 3 is a conceptual diagram of a melted vitreous silica block in a heat resistant container. It is shown that the shaded area is silica, and the white areas are gaps.

An evaluation method of an embodiment according to the present invention is an evaluation method of suitable silica powder in forming a bubble-free layer of a vitreous silica crucible for pulling of a silicon single crystal, includes: a process of measuring a porosity between the silica particles in the silica powder; a process of melting the silica powder; a process of measuring a bubble content rate of a vitreous silica block obtained by cooling to harden the melted silica powder; and a process of determining whether the silica powder is suitable from the porosity of the silica powder and the bubble content rate of the vitreous silica block. It should be noted that a vitreous silica layer which is transparent visually is called a transparent layer, and a bubble-free layer is a vitreous silica layer having a bubble content rate of 0.1 or less especially for bubbles with a diameter of 20-100 μm. Each component is explained in detail below.

1. Silica Powder

In the present invention, silica powder is synthetic silica powder or natural silica powder. Synthetic silica powder is chemically synthesized silica with an extremely low impurity concentration, and thus is used in the inner face layer of the vitreous silica crucible. The manufacturing method of the synthetic silica powder material is not particularly limited and can be exemplified as gas phase oxidation of silicon tetrachloride ($SiCl_4$) (dry synthesis method), or hydrolysis of silicon alkoxide (Si ($OR_4$)) (sol-gel method). Natural silica powder is a powder manufactured by pulverizing natural mineral mainly consisting of α-quartz.

2. Vitreous Silica Crucible

The vitreous silica crucible having an inner face layer (synthetic layer) formed from synthetic silica powder and an outer face layer (natural layer) formed from natural silica powder, is manufactured by supplying natural silica powder to a rotating mold used for manufacturing a vitreous silica crucible, further supplying synthetic silica powder on the natural silica powder, and then melting the silica powder by arc discharge heat. In the initial stage of an arc melting process, bubbles are removed by subjecting the silica powder layer to a strong depressurization, thus a transparent vitreous silica layer (transparent layer) is formed, and subsequently, a vitreous silica layer (hereafter, referred to as "bubble-containing layer") containing bubbles left by weakening the depressurization is formed.

3. Evaluation Method

Silica powder is supplied by dropping freely into a heat-resistant container under atmospheric pressure in the same manner as in the manufacturing by a rotating mold method. The silica powder protruding from the container is leveled to flatten the observation plane. Thereby, the silica powder is filling in the same manner as with the rotating mold method. The heat-resistant container is not particularly limited as long as it is a material which can withstand use at a high temperature, for example, a ceramic-based composite material or a carbon-fiber-reinforced carbon composite material (C/C composite). The size of the heat-resistant container is not particularly limited, for example, a rectangular container with a length of 10-50 mm, width of 10-50 mm, height of 10-30 mm, specifically, length 30 mm×width 40 mm×height 20 mm can be selected.

The porosity of the silica powder is measured. The voids between the silica particles can be measured in a non-contact manner by using an optical detection unit comprising a light-receiving apparatus for receiving the reflection of light irradiated on the silica powder.

The light-emitting unit may be integrated into the optical detection unit, and an external light-emitting unit may be utilized. In addition, an optical detection unit that can scan along the surface of the silica powder deposited in the heat-resistant container is preferably used, for example, performance using a confocal microscope is exemplified. A confocal microscope is preferable because it can obtain an image without blurriness. As for the irradiation light, besides visible light, ultraviolet and infrared light, such as laser light also can be used; either light may be used as long as voids between the silica particles can be detected. The light-receiving apparatus can be selected depending on the type of the irradiation light, for example, an optical camera having a light-receiving lens and an image pickup unit can be used. For the purpose of detecting the voids between the silica particles, it is preferred that only light generated at the focal point is received. For the purpose of receiving only the light generated at the focusing point, it is preferred that a pinhole is provided in front of the light detector in the light-receiving apparatus. The focal length is not particularly limited, and is preferably a depth of 0.1 mm-3 mm from the surface, for example, 0.3-1.0 mm.

As for the measurement method, as shown in FIG. 1, an objective lens 10 of the optical detection unit is provided on the surface 11 of the silica powder deposited in the heat-resistant container 12 in a non-contact manner, and the voids between the silica particles are measured by scanning along the scanning direction 13. Sample scanning mode and laser scanning mode are the other scanning modes. The sample scanning mode is a mode of driving a stage carrying the sample in XY-direction to obtain a two-dimensional image. The laser scanning mode is a mode of applying laser in XY-direction to scan on the sample two-dimensionally. Either scanning mode may be employed.

The porosities of multiple measuring points are measured, and the average value thereof may be adopted. For example, it is possible to measure three positions to obtain an average value. The measured porosity may be converted to any parameter, for example, an area, an area ratio, and a ratio. When the measurement result indicates that the voids are indistinct, the measurement may be carried out by shifting the focus in any direction of X-axis, Y-axis or Z-axis.

The porosity between the silica particles before melting is preferably 15% or less, more preferably 10% or less, further preferably 5% or less, and may be at least 1% or more. "Porosity": n can be obtained as follows; for example, wherein an area of a section is S, and a total area of a cross-sectional area of the silica powder deposited in the section is $S_p$.

Porosity: $n=((S-S_p)/S)\times 100$.

In addition, the total area of the voids is assumed as $S_n$, and can be obtained by the following formula.

Porosity: $n=(S_n/S)\times 100$.

The heat-resistant container filled in with silica powder is placed in a furnace, and the inner furnace temperature is raised to the melting temperature of the silica powder. The heat source can be selected, for example, a carbon heater. The heating rate inside the furnace is not particularly limited as long as the temperature is not changed so suddenly that the gas component in the silica powder expands to rupture. For example, the heating rate may be 50-300° C./min. The melting temperature for the silica powder is not particularly limited, and it is preferred that the temperature of the arc melting is about 1500-2600° C., for example, 1500° C., 1600° C., 1700° C., 1800° C., 1900° C., 2000° C., 2100° C., 2200° C., 2300° C., 2400° C., 2500° C. or 2600° C., and may be within the range between any two of the numerical values exemplified herein. By setting the temperature in this temperature range, the temperature condition close to the arc melting can be reproduced. Heating time is preferably from 20 hours to 60 hours, more preferably from 30 hours to 50 hours, from reaching the melting temperature. The melting of silica powder may also be performed under atmospheric pressure. By melting under atmospheric pressure, it is possible to analyze the properties of the subject silica powder in more detail. When performing it under vacuum, for example, it may be from $1.0\times 10^4$ Pa to $1.0\times 10^5$ Pa, preferably $2.0\times 10^4$ Pa.

The silica powder melt is cooled, and a bubble content rate of the vitreous silica block is measured. Cooling of the silica melt may be in accordance with the completion of heating. The measurement result obtained by the optical detection unit such as a confocal microscope is input into an image processing device, and the bubble content rate P (%) of the vitreous silica block is calculated. The image of the inner surface of the vitreous silica block is taken, and the inner surface of the vitreous silica block is divided based on a constant volume as a reference volume W1. A volume W2 occupied by bubbles is determined with respect to the reference volume W1, and calculated by P (%)=(W2/W1)× 100. The focal length is not particularly limited, and is preferably a depth of 0.1 mm-3 mm from the surface, for example, a depth of 0.3-1.0 mm.

Whether a silica powder is optimal, is evaluated from the porosity between the silica particles and the bubble content rate in the vitreous silica block. The method for evaluating whether the silica powder is optimal is not particularly limited, and when the bubble content rate of the vitreous silica block after melting with respect to the porosity between the silica particles before melting (hereinafter, it may be referred to as a contraction index of before and after melting) is preferably 0.5 or more, more preferably 0.7 or more, further preferably 0.8 or more, the silica powder is evaluated to be excellent. Such method that a silica powder of high quality can be evaluated in advance by using numbers did not exist before. On the other hand, when the contraction index before and after melting is less than 0.5, a transparent layer without bubbles may not be able to be manufactured stably. The above evaluation may be an area of pores or bubbles. Also, a result based on an area converted even when the voids or bubbles are not quantified as area, or an area calculated using other means, may be in the above range.

4. Method of Manufacturing Vitreous Silica Crucible

A vitreous silica crucible can be manufactured by (1) while rotating a mold having a bowl-shaped inner surface which defines the outer shape of the vitreous silica crucible, depositing a natural silica powder to a predetermined thickness followed by depositing a synthetic silica powder to a predetermined thickness on a bottom portion and side face inside the mold, to form a silica powder layer, (2) melting the silica powder layer by arc discharge followed by cooling.

The melting of the silica powder is preferably performed so that the maximum temperature of the inner surface of the rotating mold is up to 2000-2600° C.

The arc melting is performed, for example, by arc discharge of three-phase (R phase, S phase, T phase) alternating current. Therefore, in the case of three-phase alternating current, three carbon electrodes are used to generate arc discharge; thereby the silica powder layer is melted. The arc melting starts the arc discharge at the position where the tip of the carbon electrode is positioned higher than the opening portion of the mold. Thus, the silica powder layer near the opening portion of the mold is melted preferentially. There-after, the carbon electrode is lowered to melt the silica powder layer of the straight body portion, the corner portion, and the bottom portion.

The measurement result obtained by the optical detection unit such as a confocal microscope, is input into an image processing device, and the bubble content rate P (%) of the vitreous silica crucible is calculated. An image of the crucible inner surface is taken, and the crucible inner surface is divided based on a constant volume as a reference volume W1. A volume W2 occupied by bubbles is determined for the reference volume W1, and calculated by P (%)=(W2/W1)× 100.

EXAMPLES

1. Measurement of Voids

Example 1

A synthetic silica powder of Example 1 in a heat-resistant container was supplied to a rectangular carbon container of length 30 mm×width 40 mm×height 20 mm, and a porosity was measured by a confocal microscope. The focal length was a position of 0.3 mm from the surface. The porosity was calculated based on an arithmetic average value of the void areas at three measurement positions (the focal length was the same). The porosity at this time was 7.2%. After the porosity measurement, the heat-resistant container filled with synthetic silica powder was placed in a furnace.

The furnace using a carbon heater was heated to an inner furnace temperature of about 2200° C., to allow for melting the synthetic silica powder of Example 1 in the heat-resistant container. After melting at 2200° C. for 40 hours, the furnace was allowed to reach room temperature without being opened. The vitreous silica block was removed upon reaching room temperature, and the bubble content rate was measured to be 4.2% by the same method as that before melting.

Accordingly, it was found that, for the silica powder of Example 1, the contraction index (the bubble content of the vitreous silica block)/(the porosity of the silica particles) before and after melting was 0.58.

Example 6

A synthetic silica powder (Example 6) of a different lot from Example 1 was supplied in a heat-resistant container to a rectangular carbon container of length 30 mm×width 40 mm×height 20 mm, and the porosity was measured by a confocal microscope. The measurement method was the same as Example 1. The porosity at this time was 10.2%. After the porosity measurement, the heat-resistant container filled with synthetic silica powder was placed in a furnace.

The furnace using a carbon heater was heated to an inner furnace temperature of about 2200° C., to allow for melting the synthetic silica powder of Example 2 in the heat-resistant container. After melting at 2200° C. for 40 hours, the furnace was allowed to reach room temperature without being opened. The vitreous silica block was removed upon reaching room temperature, and the bubble content rate was measured to be 4.0% by the same method as that before melting.

Accordingly, it was found that, for the silica powder of Example 6, the contraction index before and after melting (the porosity of the vitreous silica block)/(the bubble content of the silica particles) was 0.39.

Examples 2-5, 7-10

Synthetic silica powders of a different product lot were used and the contraction indexes before and after melting were measured. Table 1 is the porosity before melting, the bubble content of the vitreous silica block, and the contraction index before and after melting relating to Examples 1-10.

TABLE 1

| | porosity before melting | bubble content of the vitreous silica block | contraction index before and after melting |
|---|---|---|---|
| Example 1 | 7.2% | 4.2% | 0.58 |
| Example 2 | 10.3% | 6.9% | 0.67 |
| Example 3 | 5.2% | 3.2% | 0.62 |
| Example 4 | 4.4% | 3.5% | 0.80 |
| Example 5 | 6.9% | 5.3% | 0.77 |
| Example 6 | 10.2% | 4.0% | 0.39 |
| Example 7 | 8.6% | 3.8% | 0.44 |
| Example 8 | 6.6% | 3.1% | 0.47 |
| Example 9 | 9.2% | 3.6% | 0.39 |
| Example 10 | 5.9% | 2.9% | 0.49 |

2. Manufacturing Vitreous Silica Crucible

Vitreous silica crucibles were manufactured using the synthetic silica powders of Examples 1-10 by the rotating mold method. The mold opening diameter was 32 inches (81.3 cm), the average thickness of silica powder layer deposited on the mold inner surface was 15 mm; arc discharge was performed with 3 electrodes using 3-phase alternating current. The energization time of the arc melting process was 90 minutes, output was 2500 kVA, and the evacuation of the silica powder layer was performed for 10 minutes from the start of energization.

Figure 4:
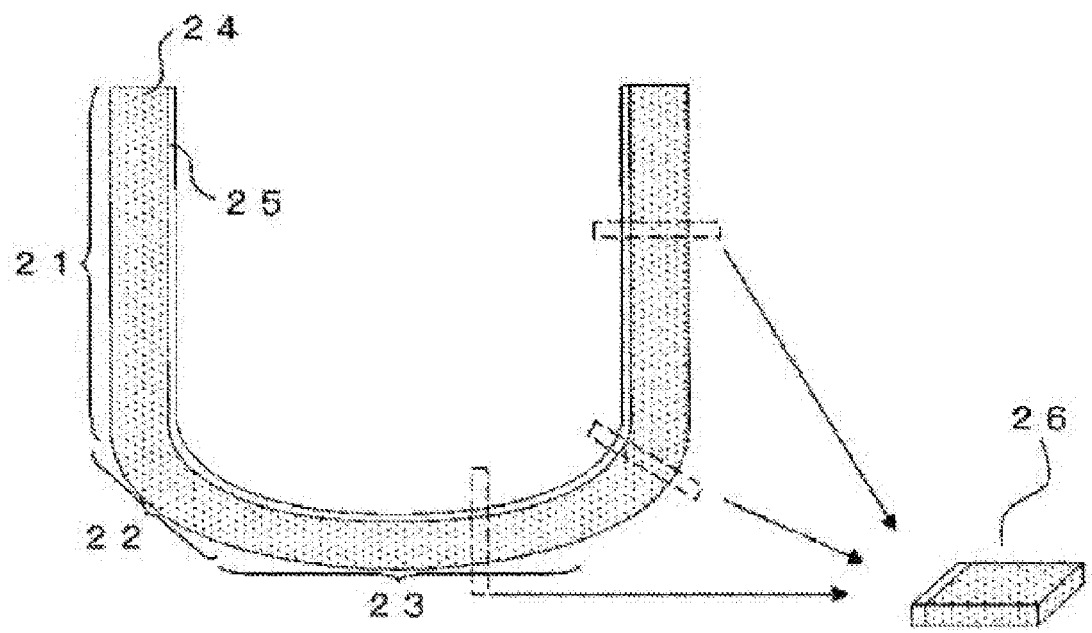
FIG. 4 is a conceptual diagram of confirming bubbles in the transparent layer of the vitreous silica crucible manufactured using synthetic silica powder.

Three vitreous silica crucibles were made by using each of the synthetic silica powders, the crucibles were sliced in the wall thickness direction as shown in FIG. 4 and polished to have a thickness of 2 mm; by this the bubbles of transparent layer 25 were confirmed. The bubble measurement was performed using a confocal microscope. The results are shown in Table 2.

Any one of the vitreous silica crucibles using the synthetic silica powders of Examples 1-5, was confirmed to be a transparent layer of a bubble-free state, and a vitreous silica crucible with a bubble-free layer could be stably manufactured. On the other hand, all five vitreous silica crucibles using the synthetic silica powders of Examples 6-10, were confirmed to have a portion with a bubble content rate of more than 0.1%, and a vitreous silica crucible with a bubble-free layer could not be stably manufactured.

Comparative Example 1

A vitreous silica crucible was made and the bubbles were measured using a confocal microscope in the same manner as described above, except that a synthetic silica powder determined to have no cause for bubble generation was used on the basis of the method described in the example of Patent Literature 2 (JP laid open 2009-007211). The results are shown in Table 2.

TABLE 2

| | Example 1 crucible No. | | | Example 2 crucible No. | | | Example 3 crucible No. | | | Example 4 crucible No. | | | Example 5 crucible No. | | |
|---|---|---|---|---|---|---|---|---|---|---|---|---|---|---|---|
| | 1-1 | 1-2 | 1-3 | 2-1 | 2-2 | 2-3 | 3-1 | 3-2 | 3-3 | 4-1 | 4-2 | 4-3 | 5-1 | 5-2 | 5-3 |
| Bottom portion (%) | ◎ | ○ | ○ | ○ | ◎ | ◎ | ◎ | ○ | ◎ | ◎ | ◎ | ○ | ○ | ○ | ◎ |
| Corner portion (%) | ○ | ○ | ○ | ○ | ◎ | ○ | ○ | ◎ | ○ | ◎ | ◎ | ◎ | ◎ | ◎ | ◎ |
| Straight body portion (%) | ○ | ◎ | ◎ | ◎ | ○ | ◎ | ○ | ○ | ◎ | ◎ | ○ | ◎ | ◎ | ◎ | ○ |

| | Example 6 crucible No. | | | Example 7 crucible No. | | | Example 8 crucible No. | | | Example 9 crucible No. | | | Example 10 crucible No. | | | Comparative Example 1 crucible No. |
|---|---|---|---|---|---|---|---|---|---|---|---|---|---|---|---|---|
| | 6-1 | 6-2 | 6-3 | 7-1 | 7-2 | 7-3 | 8-1 | 8-2 | 8-3 | 9-1 | 9-2 | 9-3 | 10-1 | 10-2 | 10-3 | 11-1 |
| Bottom portion (%) | X | ○ | ○ | ○ | ○ | ○ | ○ | ○ | ○ | X | X | ○ | ◎ | ○ | ○ | X |
| Corner portion (%) | X | ○ | X | ○ | ○ | ○ | ◎ | X | ○ | X | ○ | ○ | ○ | ○ | X | X |
| Straight body portion (%) | ○ | ○ | X | X | X | ○ | ○ | ○ | X | ○ | X | ○ | ○ | X | ◎ | X |

| ◎ | ○ | X |
|---|---|---|
| Bubble content rate <0.01 | 0.01 to 0.1 | >0.1 |

From the above results, it is apparent that by using the evaluation method of the present invention, it is possible to evaluate (judge) in advance a silica powder that does not generate bubbles in the transparent layer.

DESCRIPTION OF REFERENCE NUMERALS

10 objective lens
11 surface
12 heat-resistant container
13 scanning direction
21 straight body portion
22 corner portion
23 bottom portion
24 bubble layer
25 transparent layer
26 sliced piece

The invention claimed is:

1. An evaluation method of silica powder for forming a bubble-free layer of a vitreous silica crucible for pulling of a silicon single crystal, comprising:
    a process of measuring a porosity between silica particles in the silica powder before melting the silica powder;
    a process of melting the silica powder;
    a process of measuring a bubble content rate of a vitreous silica block obtained by cooling to harden the melted silica powder;
    a process of calculating a contraction index representing a contraction degree before and after melting the silicon powder by comparing the bubble content rate of the vitreous silica with the porosity of the silica powder; and
    a process of evaluating the silica powder by judging whether the contraction index is within a predetermined range.

2. The evaluation method according to claim 1, wherein measurements of the porosity and the bubble content rate are performed using a confocal microscope.

3. The evaluation method according to claim 1, wherein a melting temperature of the silica powder is about 1500-2600° C.

4. The evaluation method according to claim 1, wherein the contraction index is expressed as the bubble content of the vitreous silica block divided by the porosity of the silica particles, and the silica powder is evaluated to be suitable when the contraction index is 0.5 or more.

5. A method of manufacturing a vitreous silica crucible, comprising the steps of:
    selecting a suitable silica powder for forming a bubble-free layer of the vitreous silica crucible using the evaluation method according to claim 1; and
    manufacturing the vitreous silica crucible by arc melting method using the suitable silica powder.

6. A method of manufacturing a vitreous silica crucible, comprising the steps of:
    selecting a suitable silica powder for forming a bubble-free layer of the vitreous silica crucible using the evaluation method according to claim 2; and
    manufacturing the vitreous silica crucible by arc melting method using the suitable silica powder.

7. A method of manufacturing a vitreous silica crucible, comprising the steps of:
    selecting a suitable silica powder for forming a bubble-free layer of the vitreous silica crucible using the evaluation method according to claim 3; and manufacturing the vitreous silica crucible by arc melting method using the suitable silica powder.

8. A method of manufacturing a vitreous silica crucible, comprising the steps of:

selecting a suitable silica powder for forming a bubble-free layer of the vitreous silica crucible using the evaluation method according to claim 4; and manufacturing the vitreous silica crucible by arc melting method using the suitable silica powder.

\* \* \* \* \*